(12) United States Patent
Pecherer

(10) Patent No.: US 7,909,759 B2
(45) Date of Patent: Mar. 22, 2011

(54) HANDHELD PENKNIFE-LIKE LARYNGOSCOPE

(75) Inventor: Eugeny Pecherer, Netanya (IL)

(73) Assignee: Truphatek International Ltd (IL)

( * ) Notice: Subject to any disclaimer, the term of this patent is extended or adjusted under 35 U.S.C. 154(b) by 971 days.

(21) Appl. No.: 11/791,113

(22) PCT Filed: Nov. 22, 2005

(86) PCT No.: PCT/IL2005/001232
§ 371 (c)(1),
(2), (4) Date: May 21, 2007

(87) PCT Pub. No.: WO2006/056976
PCT Pub. Date: Jun. 1, 2006

(65) Prior Publication Data
US 2008/0004498 A1    Jan. 3, 2008

Related U.S. Application Data

(60) Provisional application No. 60/629,894, filed on Nov. 23, 2004.

(51) Int. Cl.
*A61B 1/267* (2006.01)
(52) U.S. Cl. ........................................ 600/193; 600/199
(58) Field of Classification Search .......... 600/185–200; 81/177.9; 403/95; 30/339, 329
See application file for complete search history.

(56) References Cited

U.S. PATENT DOCUMENTS

| | | | | |
|---|---|---|---|---|
| 330,139 | A * | 11/1885 | Meyer | 600/241 |
| 744,271 | A * | 11/1903 | Adams | 81/177.9 |
| 846,495 | A * | 3/1907 | Morley | 403/95 |
| 967,889 | A * | 8/1910 | Dethlefs et al. | 81/177.9 |
| 1,785,343 | A * | 12/1930 | Gilbert | 403/95 |
| 2,433,705 | A | 12/1947 | Palmeter | |
| 3,426,749 | A | 2/1969 | Jephcott | |

(Continued)

FOREIGN PATENT DOCUMENTS

DE    26 21 232    11/1977

(Continued)

OTHER PUBLICATIONS

Hilbro brochure, Green System Fiber Optic Laryngoscope, Interchangeable Light Guide Insert, Oct. 2001.

(Continued)

*Primary Examiner* — Eduardo C Robert
*Assistant Examiner* — Jan Christopher Merene
(74) *Attorney, Agent, or Firm* — Hershkovitz & Associates, LLC; Abraham Hershkovitz; Harold L. Novick

(57) ABSTRACT

A handheld penknife-like laryngoscope including a handle having an electrically insulating rigid plastic blade support section and a battery compartment section for housing a power source with a pair of opposite polarity terminals including a first terminal adjacent the blade support section and a second terminal remote therefrom, and an electrically conducting metal blade non-detachably pivotally hinged on the blade support section for manipulation from an inoperative storage position co-directional with the handle to an operative intubation position perpendicular thereto. The blade tapers towards a tip and has a light source there toward with a first electrode in electrical contact with the blade and a second electrode in electrical contact with the second terminal. The laryngoscope includes a blade retaining mechanism for securely retaining the blade in the intubation position whereupon the blade is in electrical contact with the first terminal for energizing the light source.

2 Claims, 8 Drawing Sheets

U.S. PATENT DOCUMENTS

| | | | | |
|---|---|---|---|---|
| 3,598,113 | A | 8/1971 | Moore et al. | |
| 3,638,644 | A * | 2/1972 | Reick | 600/191 |
| 3,766,909 | A | 10/1973 | Ozbey | |
| 3,779,655 | A * | 12/1973 | Toyota | 403/93 |
| 3,826,248 | A | 7/1974 | Gobels | |
| 4,037,588 | A | 7/1977 | Heckele | |
| 4,124,939 | A * | 11/1978 | Onoue | 30/161 |
| 4,273,112 | A * | 6/1981 | Heine et al. | 600/193 |
| 4,406,280 | A | 9/1983 | Upsher | |
| 4,425,709 | A * | 1/1984 | Quenzi | 30/151 |
| 4,437,458 | A | 3/1984 | Upsher | |
| 4,556,052 | A | 12/1985 | Muller | |
| 4,557,256 | A * | 12/1985 | Bauman | 600/193 |
| 4,565,187 | A | 1/1986 | Soloway | |
| 4,570,614 | A | 2/1986 | Bauman | |
| 4,579,108 | A | 4/1986 | Bauman | |
| 4,583,527 | A | 4/1986 | Musicant et al. | |
| 4,596,239 | A | 6/1986 | Bauman | |
| 4,679,547 | A | 7/1987 | Bauman | |
| 4,878,486 | A | 11/1989 | Slater | |
| 4,884,558 | A | 12/1989 | Gorski et al. | |
| 4,930,495 | A | 6/1990 | Upsher | |
| 4,958,624 | A | 9/1990 | Stone et al. | |
| 4,972,825 | A | 11/1990 | Vescovo, Jr. | |
| 5,060,633 | A | 10/1991 | Gibson | |
| 5,065,738 | A | 11/1991 | Van Dam | |
| 5,095,624 | A * | 3/1992 | Ennis | 30/161 |
| 5,169,257 | A * | 12/1992 | Liou | 403/95 |
| 5,178,131 | A | 1/1993 | Upsher | |
| 5,355,870 | A | 10/1994 | Lacy | |
| 5,501,651 | A | 3/1996 | Bauman | |
| 5,529,570 | A | 6/1996 | Storz | |
| 5,651,760 | A | 7/1997 | Upsher | |
| 5,685,079 | A * | 11/1997 | Brothers et al. | 30/161 |
| 5,702,351 | A * | 12/1997 | Bar-Or et al. | 600/190 |
| 5,769,094 | A * | 6/1998 | Jenkins et al. | 30/161 |
| 5,873,818 | A * | 2/1999 | Rothfels | 600/188 |
| 5,879,304 | A | 3/1999 | Shuchman et al. | |
| 6,013,026 | A * | 1/2000 | Krauter et al. | 600/193 |
| 6,139,491 | A | 10/2000 | Heine et al. | |
| 6,213,937 | B1 | 4/2001 | Vivenzio | |
| 6,354,993 | B1 * | 3/2002 | Kaplan et al. | 600/188 |
| 6,719,688 | B2 | 4/2004 | Pecherer et al. | |
| 6,918,184 | B2 * | 7/2005 | Glesser | 30/161 |
| 6,964,637 | B2 * | 11/2005 | Dalle et al. | 600/193 |
| 7,007,392 | B2 * | 3/2006 | Ping | 30/156 |
| 7,128,710 | B1 | 10/2006 | Cranton et al. | |
| 7,214,184 | B2 | 5/2007 | McMorrow | |
| 7,338,440 | B1 * | 3/2008 | Smith | 600/187 |
| 2002/0082478 | A1 | 6/2002 | McGrath | |
| 2004/0034281 | A1 * | 2/2004 | Cartledge et al. | 600/190 |
| 2004/0215062 | A1 * | 10/2004 | Dalle et al. | 600/193 |
| 2005/0234303 | A1 * | 10/2005 | McMorrow | 600/189 |
| 2010/0261968 | A1 * | 10/2010 | Nearman et al. | 600/188 |

FOREIGN PATENT DOCUMENTS

| | | |
|---|---|---|
| DE | 202 18 560 | 7/2003 |
| EP | 0184588 | 6/1986 |
| EP | 0653180 | 10/1998 |
| GB | 685741 | 1/1953 |
| GB | 806467 | 12/1958 |
| GB | 2437435 | 8/2009 |

OTHER PUBLICATIONS

Medizintechnik KaWe Germany, Laryngoscopes, Megalight F.O.

* cited by examiner

HANDHELD PENKNIFE-LIKE LARYNGOSCOPE

CROSS-REFERENCE TO RELATED APPLICATIONS

This application is the national stage filing of PCT International Application Serial Number PCT/IL2005/001232 filed 22 Nov. 2005, which in turn claims priority on U.S. Provisional Application No. 60/629,894 filed 23 Nov. 2004; both which are incorporated in their entireties herein by reference.

FIELD OF THE INVENTION

The present invention pertains to penknife-like laryngoscopes.

BACKGROUND OF THE INVENTION

Conventional penknife-like laryngoscopes have metal handles with metal blades non-detachably pivotally hinged thereon for swinging from an inoperative storage position generally co-directional to their handles to an operative intubation position generally perpendicular thereto. The blades taper toward tips and have bulbs theretowards for illumination purposes. The laryngoscopes are typically designed to automatically energize their bulbs in their intubation position.

SUMMARY OF THE INVENTION

The present invention is for a handheld penknife-like laryngoscope including a handle having an electrically insulating rigid plastic blade support section and a power source compartment section for housing a power source with a pair of opposite polarity terminals including a first terminal adjacent the blade support section and a second terminal remote therefrom, and an electrically conducting metal blade non-detachably pivotally hinged on the blade support section for manipulation from an inoperative storage position generally co-directional with the handle to an operative intubation position generally perpendicular thereto. The blade tapers towards a tip and has a light source theretowards with a first electrode in electrical contact with the blade and a second electrode in electrical contact with the second terminal by way of an electrically insulated wire. The laryngoscope includes a blade retaining mechanism for securely retaining the blade in its intubation position whereupon the blade is in electrical contact with the first terminal for energizing the light source. The electrically insulating rigid plastic blade support section of the penknife-like laryngoscope in accordance with the present invention affords a lower cost design than conventional all metal penknife-like laryngoscopes such that penknife-like laryngoscopes in accordance with the present invention are particularly suitable for single use disposable laryngoscopes. The blade retaining mechanism can include snap fit arrangements, thumb operated arrangements, and the like.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DESCRIPTION OF THE PREFERRED EMBODIMENTS OF THE PRESENT INVENTION

Figure 1:
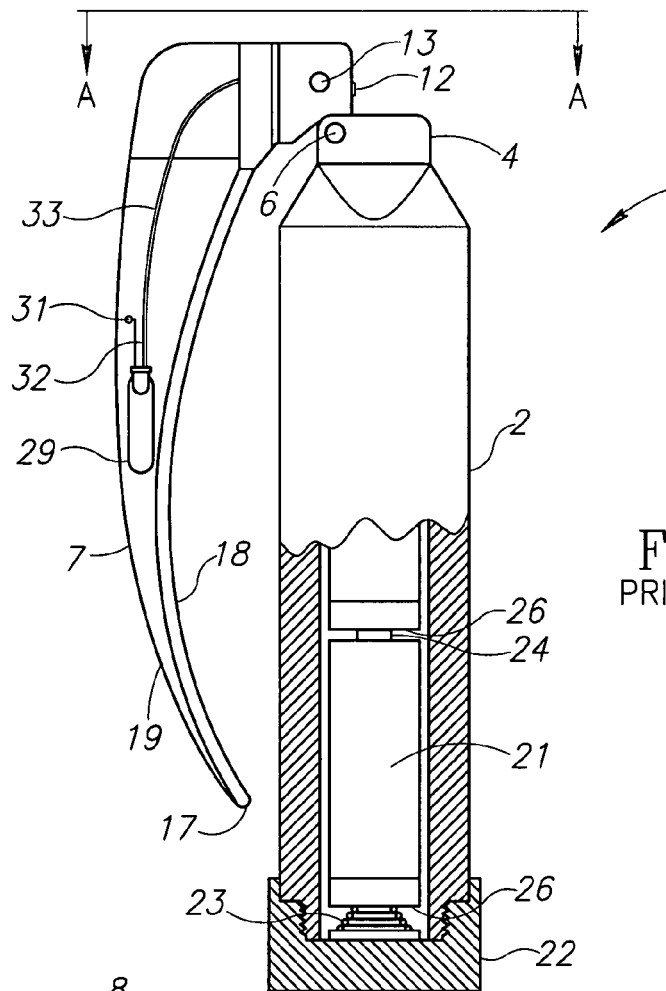
FIG. 1 is a pictorial view of a conventional all metal penknife-like laryngoscope.
Figure 2:
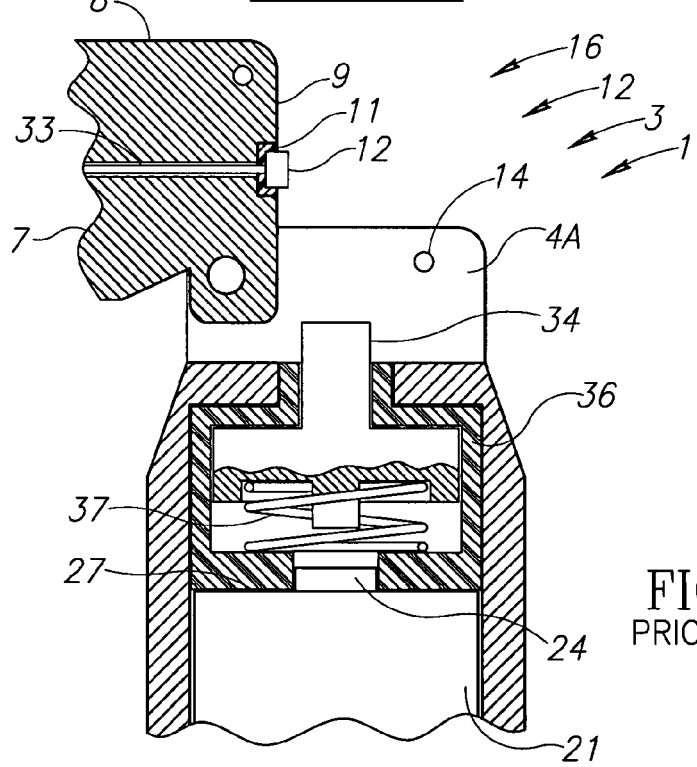
FIG. 2 is a longitudinal cross section of the upper part of FIG. 1's laryngoscope along line A-A in FIG. 1.
Figure 3:
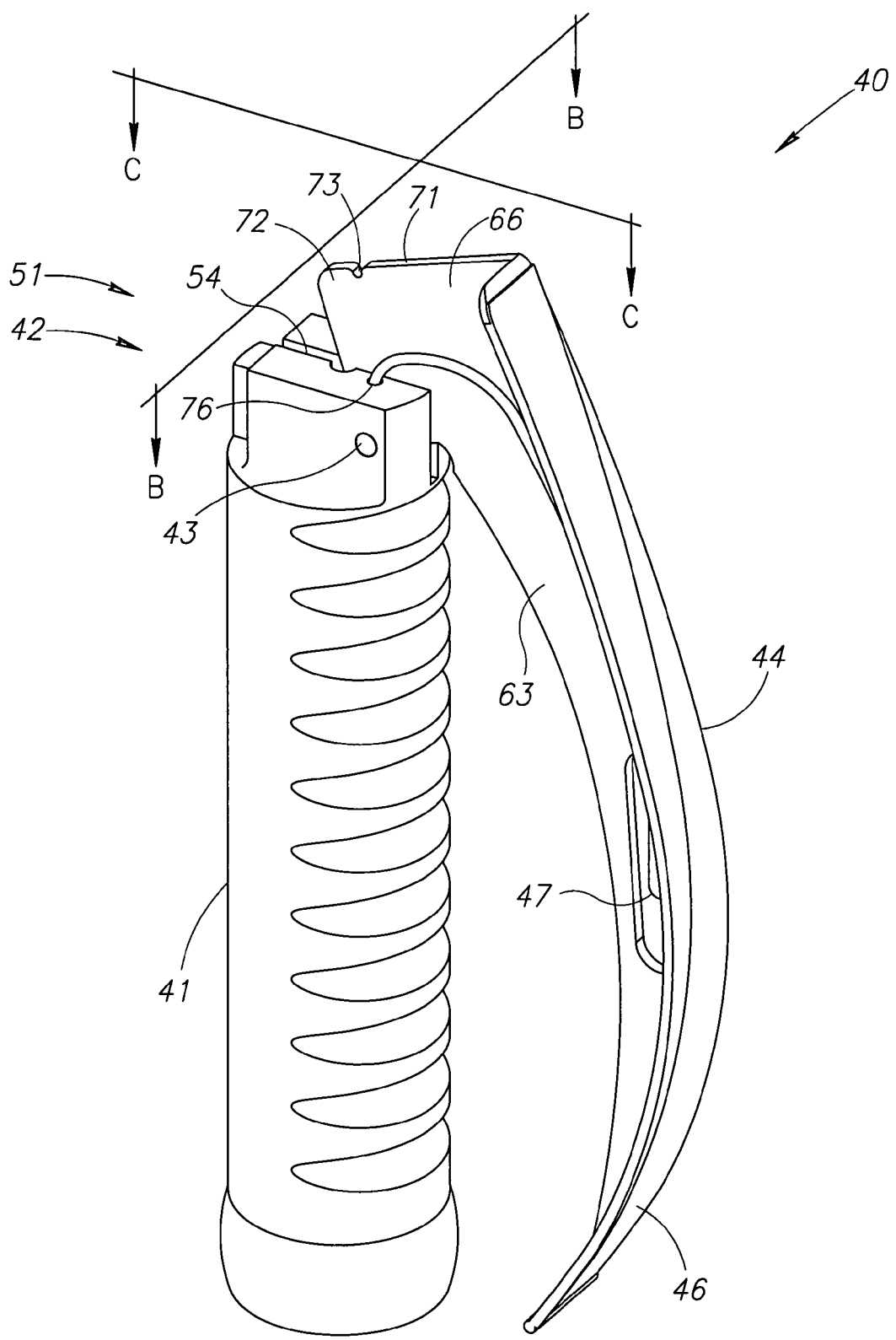
FIG. 3 is a pictorial view of a penknife-like laryngoscope with an all plastic handle in accordance with the present invention in its inoperative storage position.
Figure 4:
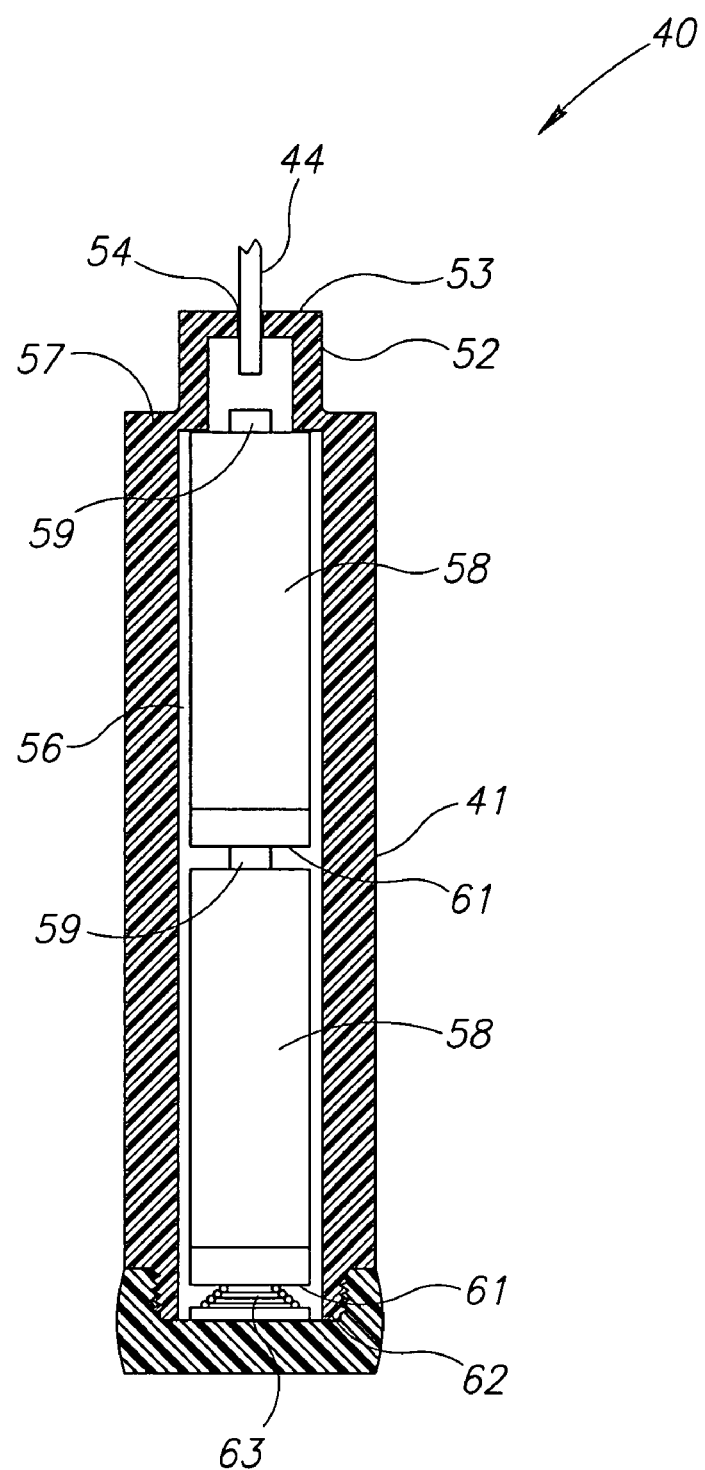
FIG. 4 is a longitudinal cross section of FIG. 3's laryngoscope along line B-B in FIG. 3 with its blade in its inoperative storage position.
Figure 5:
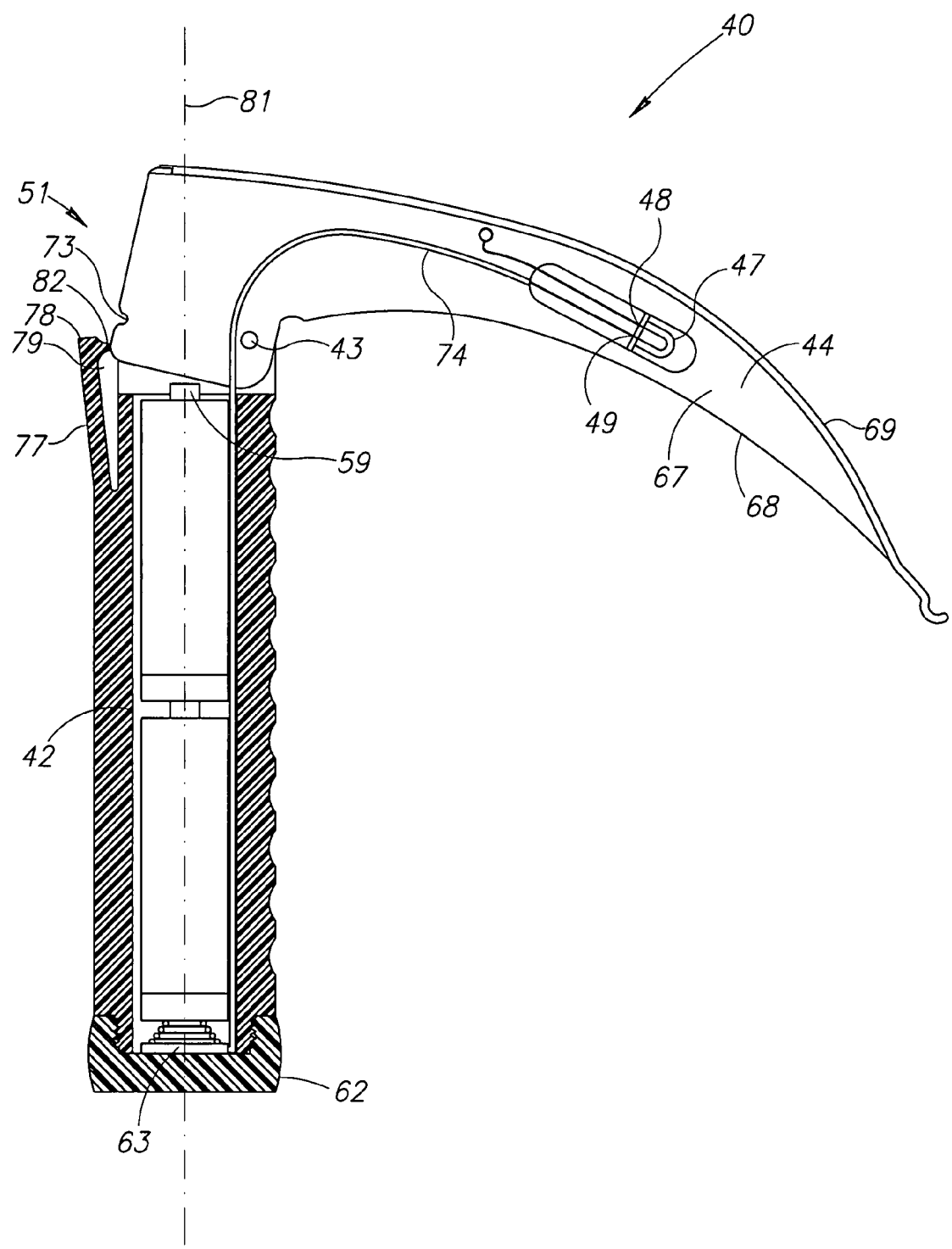
FIG. 5 is a longitudinal cross section of FIG. 3's laryngoscope along line C-C in FIG. 3 with its blade midway between its inoperative storage position and its operative intubation position.
Figure 6:
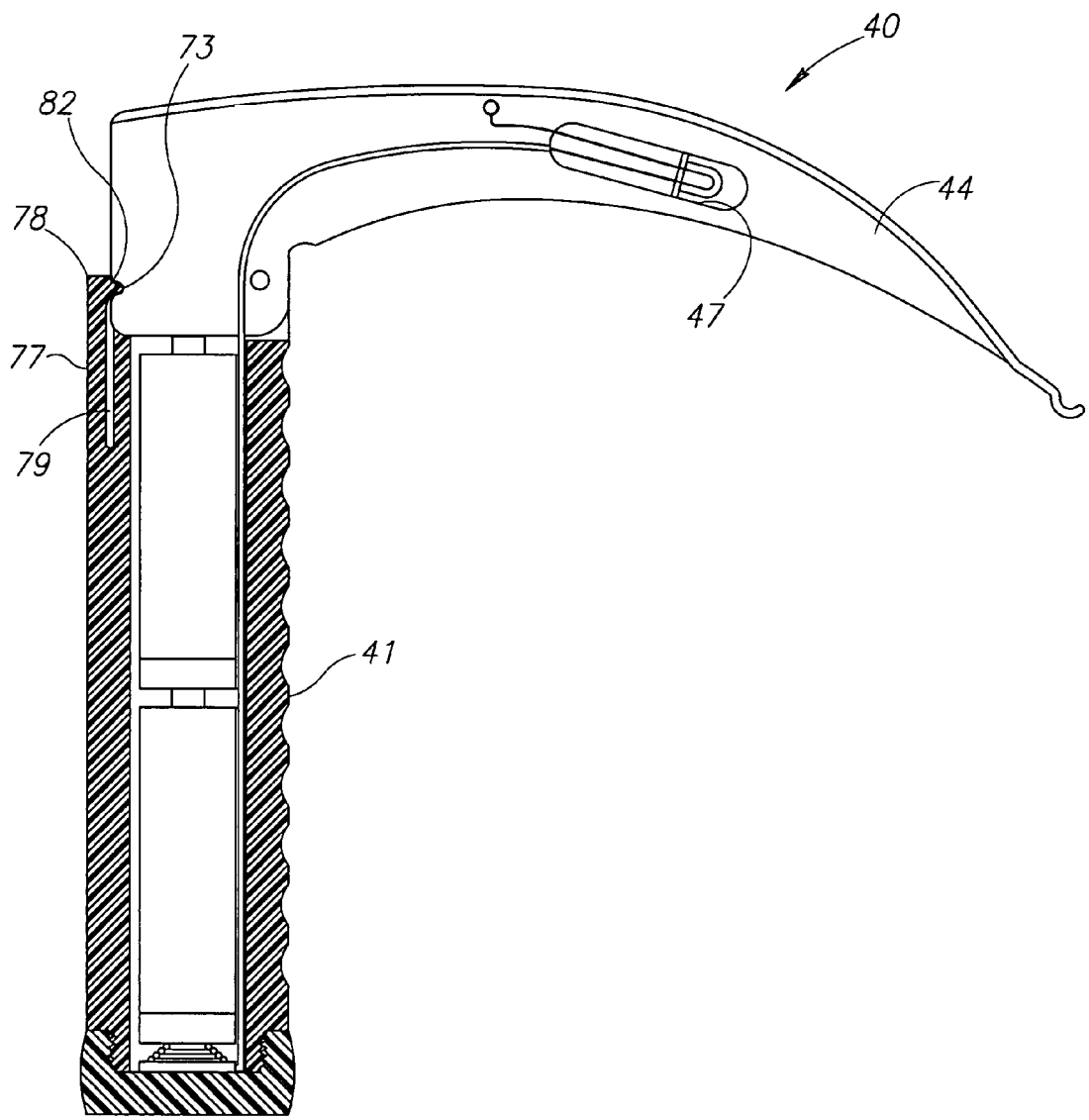
FIG. 6 is a longitudinal cross section of FIG. 3's laryngoscope along line C-C in FIG. 3 with its blade in its operative intubation position.
Figure 7:
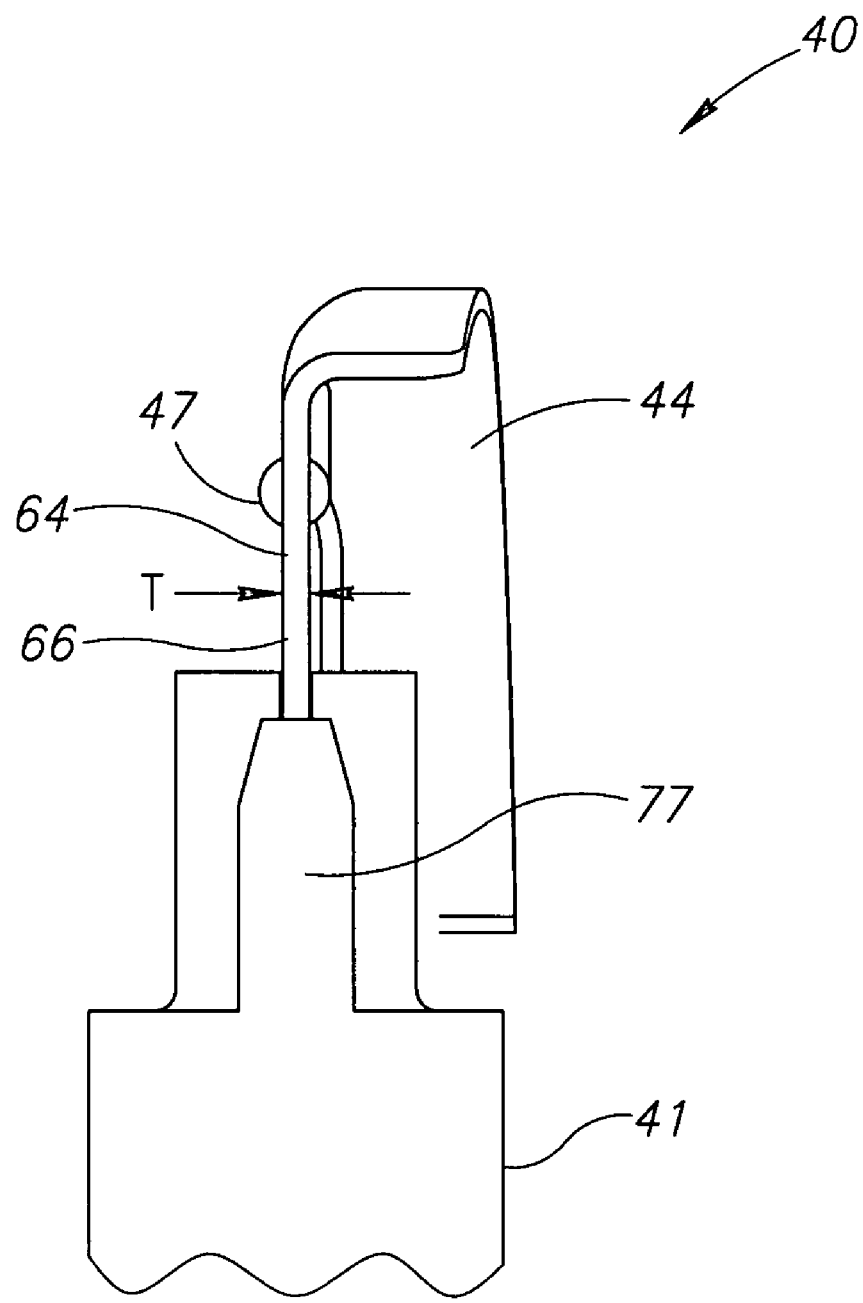
FIG. 7 is a rear view of FIG. 3's laryngoscope with its blade in its operative intubation position.

FIGS. 1 and 2 show a laryngoscope 1 with a metal handle 2 with a blade support section 3 in the form of a pair of opposite and parallel side walls 4 with a pivot rod 6 extending thereacross, and a metal blade 7 with a base portion 8 non-detachably pivotally hinged on the handle 2 between an inoperative storage position with the blade 7 generally co-directional with the handle 2 and an operative intubation position with the blade 7 generally perpendicular thereto. The handle 2 and blade 7 are formed from a suitable metal such as stainless steel, and the like. The base portion 8 has an underside 9 with an electrically insulating bushing 11 protecting a metal contact 12. The base portion 8 is fitted with a pair of spring mounted ball bearings 13 for snap fitting into recesses 14 formed in the side walls' inside surfaces 4A together constituting a blade retaining mechanism 16 for retaining the blade 7 in its intubation position. The blade 7 tapers towards a tip 17 and includes a tongue engaging surface 18 and an opposite flange-like teeth engaging surface 19.

The handle 2 stores two C-sized batteries 21 in series (constituting a power source) and is closed by a metal cap 22 having a metal compression spring 23 for urging the batteries 21 towards the blade 7. The batteries 21 are intended to be inserted with their positive terminals 24 directed toward the blade 7 and their negative terminals 26 directed away therefrom. The blade 7 is fitted with a bulb 29 having two electrodes 31 and 32. The electrode 31 is soldered to the blade 7 and consequently in electrical contact with the trailing battery's negative terminal 26 via the handle, the cap 22, and the compression spring 23. The electrode 32 is connected to the metal contact 12 via an electrically insulated wire 33. The handle 2 includes a metal contact pin 34 slidingly mounted in a tubular electrically insulating bushing 36 including a compression spring 37 for outwardly urging the metal contact pin 34 away from the leading battery's positive terminal 24.

Manipulation of the blade 7 from its storage position to its intubation position presses the metal contact 12 against the contact pin 34 which in turn contacts the leading battery's positive terminal 24 to energize the bulb 29 for illumination purposes. Release of the blade 7 from its intubation position breaks the electrical contact to cease energizing the bulb 29.

FIGS. 3-7 show a penknife-like laryngoscope 40 similar in construction and operation to the penknife-like laryngoscope 1 insofar that the laryngoscope 40 has a handle 41 with a blade support section 42 with a pivot rod 43 extending thereacross, and an electrically conducting metal blade 44 non-detachably pivotally hinged on the handle 41 for selective manipulation from an inoperative storage position to an operative intubation position. The blade 44 tapers towards a tip 46 and includes a light source 47 theretoward. The light source 47 has a pair of electrodes 48 and 49 can be energized by a power source in the form of batteries, a rechargeable power pack, and the like, depending on the size of the handle, the required illumination, etc. The light source 47 can be in the form of an incandescent bulb, a Light Emitting Diode (LED), and the like. The laryngoscope 40 includes a blade retaining mechanism 51 for retaining the blade 44 in its intubation position for automatically energizing the light source 47.

The laryngoscope 40 differs from the laryngoscope 1 insofar that the former includes an all plastic handle made from electrically insulating material, for example, PVC, polyamide, and the like. The handle 41 has a stepped configuration including a neck portion 52 with a top surface 53 having a diametrical blade receiving slit 54 for snugly receiving the blade 44 in its intubation position, a battery compartment 56 for housing a power source, and an annular shoulder 57 connecting the neck portion 52 and the battery compartment 56. The shoulder 57 enables a power source to be inserted with either polarity terminal toward the blade 44 without effecting operation of the laryngoscope 40. For illustration purposes, the laryngoscope 40 is powered by a pair of AA size batteries 58 inserted with their positive terminals 59 towards the blade 44 and their negative terminals 61 remote therefrom. The handle 41 includes a plastic screw on cap 62 with a compression spring 63 for urging the batteries 58 against the shoulder 57 whereupon the leading battery's positive terminal 59 directly underlies the blade receiving slit 54 whereupon it is visible therethrough in the blade's storage position.

The blade 44 includes a thin upright member 64 with a thin trailing portion 66 non-detachably pivotally hinged on the pivot rod 43, and a leading tapering tongue depressor portion 67 with a tongue engaging surface 68 and an opposite flange-like teeth engaging surface 69, and the light source 47. The trailing portion 66 includes a rearmost surface 71 with a blade corner 72 opposite the pivot rod 43, and a notch 73 above the blade corner 72. The upright member 64 including its trailing portion 66 have a thickness T of preferably less than 1.5 mm, say, about 1.2 mm. The blade receiving slit 54 is slightly wider than the trailing portion 66, say, by about +0.1 mm, to snugly receive same.

The electrode 48 is in electrical contact with the blade 44 and can be soldered thereto, pressed thereagainst, and the like. The electrode 49 is in electrical contact with the trailing battery's negative terminal 61 by way of an electrically insulated wire 74 passing through a throughgoing bore 76 formed in the top surface 53. The wire 74 is provided with sufficient slack to enable the blade's swinging action from its inoperative storage position to its operative intubation position.

The blade retaining mechanism 51 includes a longitudinally directed leaf spring retaining member 77 with a free end 78 formed by a longitudinally directed slot 79 offset with respect to the handle's longitudinal axis 81. The leaf spring retaining member 77 is resiliently flexibly displaceable between a natural upright position in both a blade's storage position and intubation position, and an elastically deformed position with its free end 78 outwardly urged with respect to the longitudinal axis 81. The free end 78 is formed with a detent 82 for snap fitting into the blade's notch 73 for retaining the blade 44 in its intubation position and urging the blade 44 to bear against the leading battery's positive terminal 59 for energizing the light source 47. In this position, the blade 44 depresses the batteries 58 against the compression spring 63 to slightly compress same thereby leaving a slight gap between the leading battery's top surface and the shoulder 57.

Figure 8:
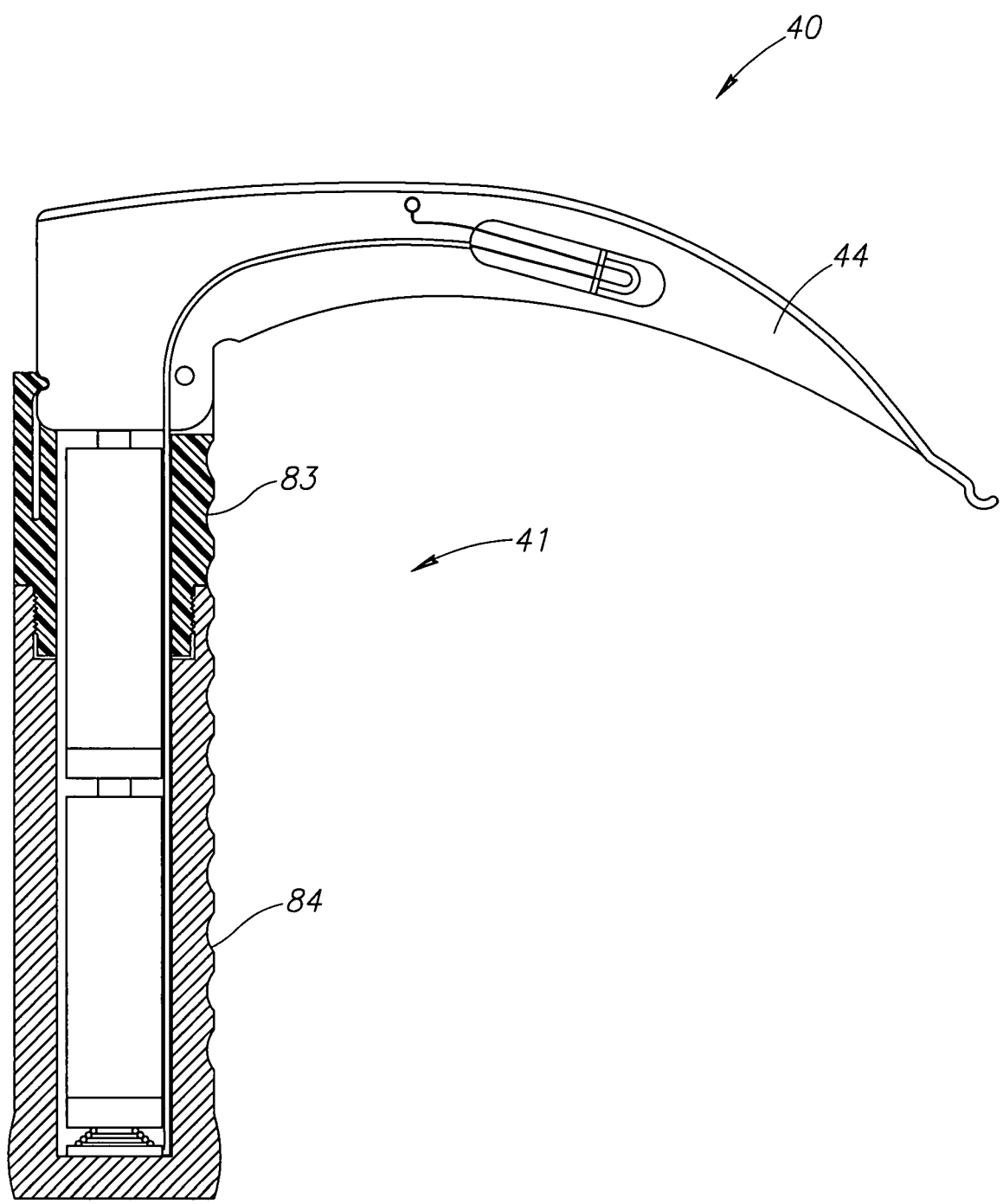
FIG. 8 is a longitudinal cross section of a penknife-like laryngoscope in accordance with the present invention with a handle including a metal power source compartment section.

FIG. 8 shows a laryngoscope 40 with a non all plastic handle 41 including a plastic blade support section 83 and a metal power source compartment section 84 for screw threading onto the plastic blade support section 83.

Figure 9:
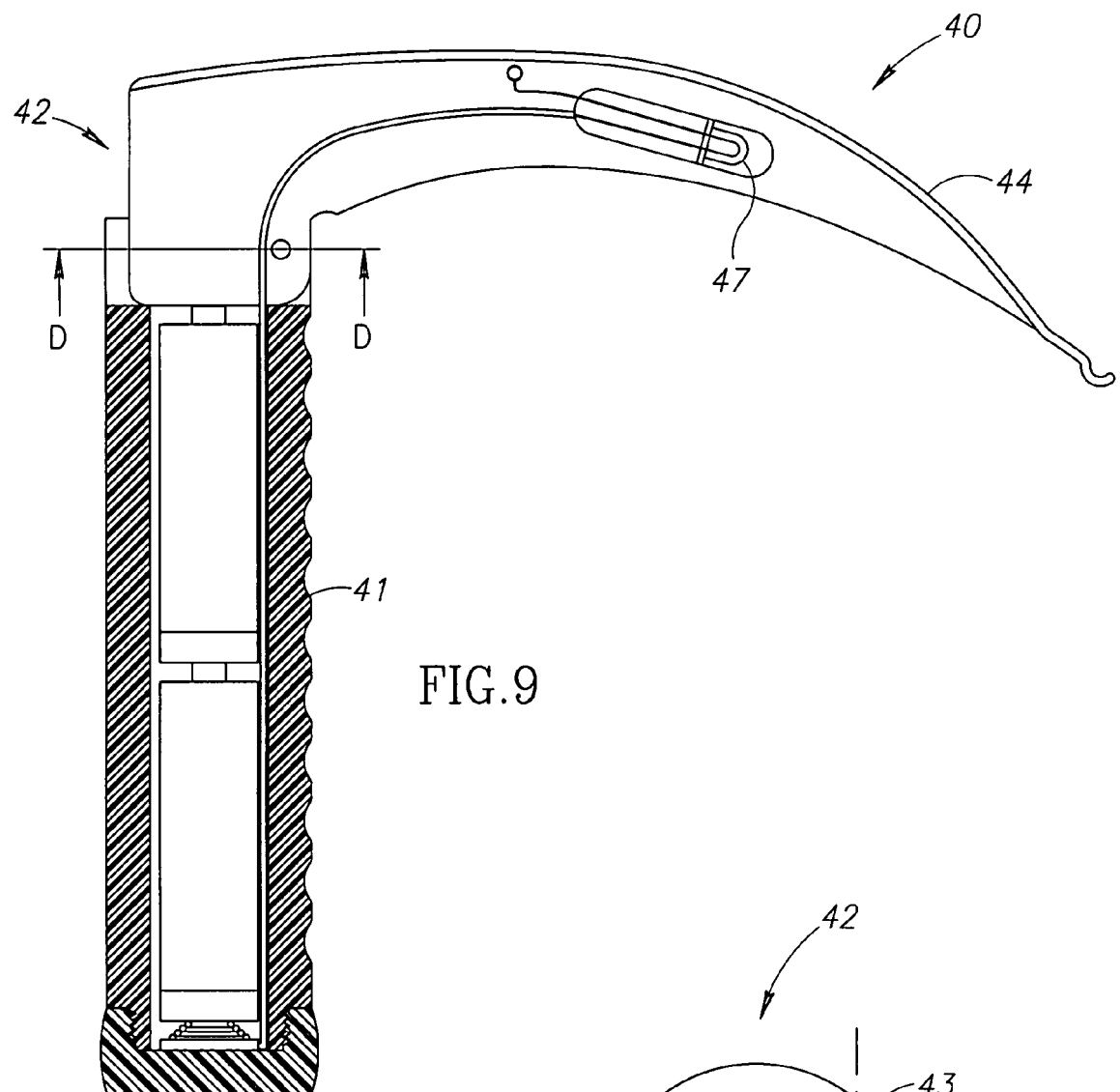
FIG. 9 is a longitudinal cross section of a penknife-like laryngoscope in accordance with the present invention with an alternative blade retaining mechanism.
Figure 10:
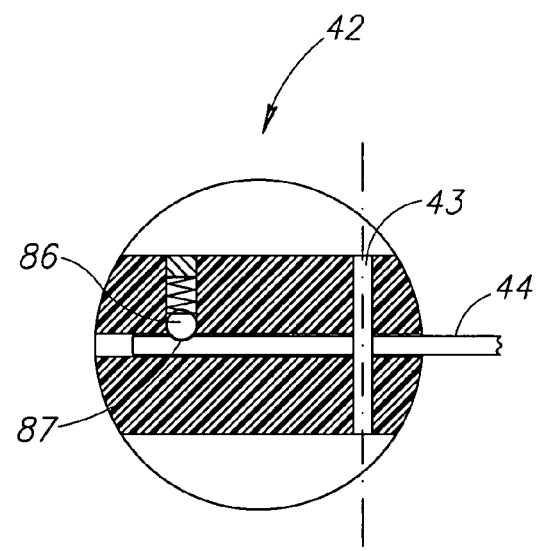
FIG. 10 is a transverse cross section of FIG. 9's laryngoscope along line D-D in FIG. 9.

FIGS. 9 and 10 show a laryngoscope 40 with a blade support section 42 including a spring mounted ball bearing 86 for snap fitting into a recess 87 formed in the blade 44 in its intubation position for retaining the blade 44 therein for energizing the light source 47.

The use of the penknife-like laryngoscope 40 is as follows:

A user holds the handle in one hand and swings the blade from its inoperative storage position to its intubation position with his other hand. The blade corner bears against the detent during the swinging action to initially urge the leaf spring retaining member outwards with respect to the longitudinal axis (see FIG. 5) until the blade corner passes the detent whereupon the leaf spring retaining member snap backs to its natural upright position and the detent snap fits into the notch (see FIGS. 6 and 7). The snap fitting of the detent into the notch urges the blade to directly contact the leading battery's positive terminal for energizing the light source for illumination purposes whereupon the laryngoscope is ready for use.

While the invention has been described with respect to a limited number of embodiments, it will be appreciated that many variations, modifications, and other application of the present invention can be made within the scope of the appended claims.

The invention claimed is:

1. A handheld penknife-like laryngoscope comprising:
   a. an all plastic handle having an electrically insulating rigid plastic blade support section that includes a diametrical blade receiving slit, a neck portion, a rigid plastic power source compartment section integrally formed with said blade support section for housing a power source when installed, said power source having a pair of opposite polarity terminals including a first terminal adjacent said blade support section and a second terminal remote therefrom, and a shoulder connecting said neck portion and said power source compartment section for abutment of a power source there against when housed in said power source compartment section;
   b. an electrically conducting metal blade tapering toward a tip, and including a trailing portion non-detachable pivotally hinged on said blade support section for manipulation from an inoperative storage position generally co-directional with said handle to an operative intubation position generally perpendicular thereto, said blade trailing portion being received in said slit in said intubation position and when in said intubation position results in electrical contact with said first terminal;
   c. a light source mounted towards said tip, and having a pair of electrodes including
   a first electrode mounted to said blade and in electrical contact with a first terminal of a power source when the power source is installed and when said blade is in said intubation position, and a second electrode in direct electrical contact with an electrically insulated wire which in turn is in direct electrical contact in both the storage position and the intubation position of said blade with said second terminal of the power source when installed; and d. a blade retaining mechanism for securely retaining said blade in said intubation position, said blade retaining mechanism comprising a leaf spring retaining member in said blade support section with a free end directed towards said blade and formed with a detent for snap fitting into a notch on a rearmost surface of said blade when in said intubation position, whereupon when said blade is in said intubation position, said light source is automatically energized.

2. A laryngoscope as claimed in claim 1, wherein said first electrode is in electrical contact with said blade, and when said metal blade trailing portion is received in said slit in said intubation position, said blade directly contacts said first terminal of the power source when installed and is in electrical contact therewith, thereby automatically energizes said light source.

\* \* \* \* \*